June 11, 1974 A. BARBERET Plant Pat. 3,570
CARNATION PLANT (LONRINA)
Filed Nov. 10, 1972
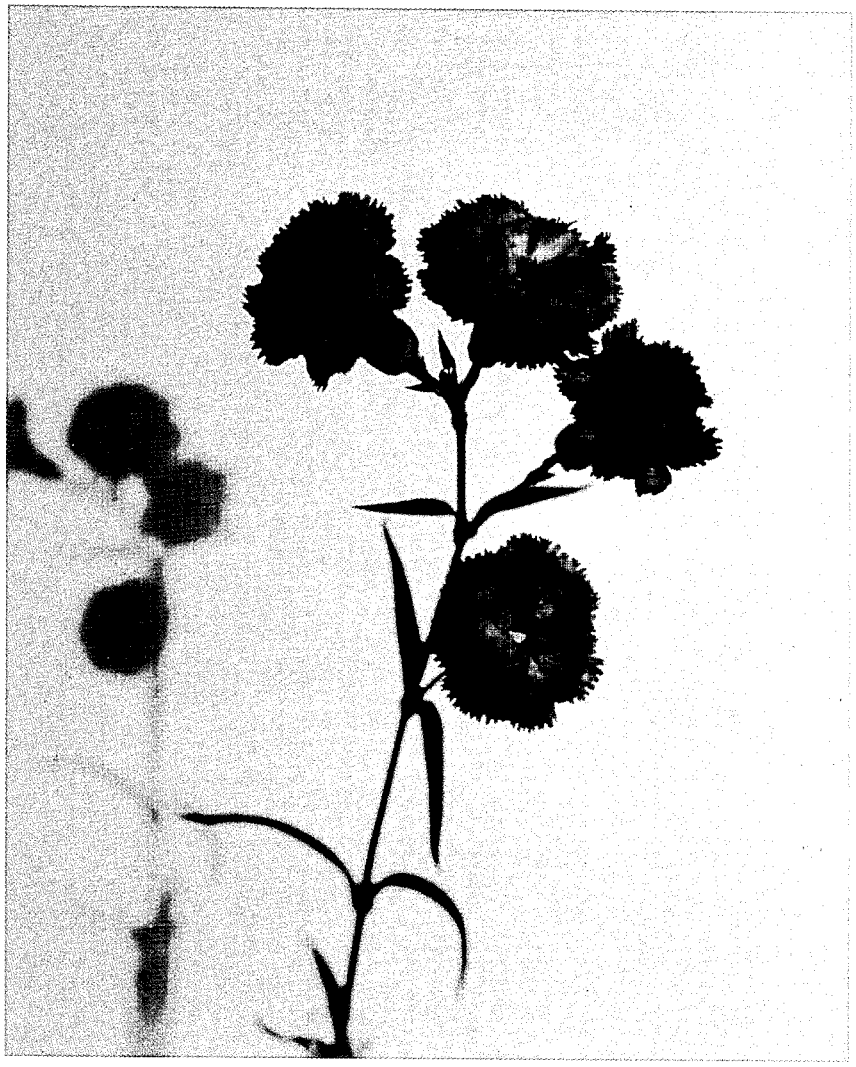

United States Patent Office

Plant Pat. 3,570
Patented June 11, 1974

3,570

CARNATION PLANT

Alexandre Barberet, La Londe-les-Maures, France, assignor to Laboratoire de Physiologie Vegetale de La Londe Societe Civile Agricole, La Londe-les-Maures, France Filed Nov. 10, 1972, Ser. No. 305,341
Int. Cl. A01h 5/00
U.S. Cl. Plt.—73 1 Claim

ABSTRACT OF THE DISCLOSURE

A new variety of carnation plant originated as a hybrid seedling produced as a cross of laboratory breeding stock and distinguished by its unusual branched growth having longer stem capability, good spray arrangement and well formed, more fragrant blossoms.

BACKGROUND OF THE NEW PLANT

My new variety of carnation plant is the result of extensive breeding efforts carried on by me at La Londe, France, since 1969, with the objective of producing an improved carnation plant having a higher wintertime production with vigorous and high branching growth habit and having better color stability in its blossoms. This seedling was selected for propagation and test because it appeared to exhibit the desired characteristics and my asexual propagation of this plant, by means of cuttings, through many generations at La Londe, France, has demonstrated that the distinctive and desirable features of this new plant are firmly fixed and remain true from generation to generation.

DESCRIPTION OF THE DRAWINGS

My new variety of carnation plant is illustrated by the accompanying photographic drawings which show the form and growth characteristics of the plant and the form and development of its blossoms.

DESCRIPTION OF THE NEW PLANT

The following is a detailed description of my new variety of carnation plant with color designations according to The RHS Colour Chart issued by The Royal Horticultural Society at London, England.

THE PLANT

Origin: Seedling
Parentage:
*Seed parent.*—Carnation 191V (unnamed, unpatented).
*Pollen parent.*—Carnation 230R (unnamed, unpatented).
Classification:
*Botanic.*—Hybrid of *Dianthus caryophyllus* L.
*Commercial.*—Miniature carnation for cut flowers.
Form: Leafy and like the Sim types.
Height: About 65 cm. for the one-year, five-month old plant.
Growth: Vigorous and erect with upright, high branching.
Foliage:
*Quantity.*—Abundant.
*Leaf shape.*—Lanceolate, amplexicaul and up to 14 cm. long.
*Texture.*—Smooth.

*Color.*—Upper side—Greyed-Green Group 189A to 191A. Under side—Same Green coloring.
*Ribs.*—One axial rib well visible on the under side.

THE BUD

Form: Ovoid, becoming cylindrically ovoid when sepals first divide.
Size: Medium. Diameter: Up to 1.3 cm. Depth: Up to 2.8 cm.
Opening: Bud opens slowly.
Color: Light Green when sepals first divide and when the petals begin to unfurl.
Sepals: Stand up.
*Color.*—Inside—Pale Green. Outside—Light Green.
Calyx:
*Shape.*—Funnel-like, long, and does not split.
*Aspect.*—Smooth.

THE FLOWER

Blooming habit: This plant blooms continuously and profusely.
Size of bloom: Medium, averaging 5.3 cm. in diameter and 2.7 cm. in depth.
Borne: Singly in spray arrangement of stems.
Shape: Flat. Form does not change as blossom matures.
Petalage: Number of petals—36 to 45, with average about 40.
*Arrangement.*—Tendency to be imbricated.
*Form.*—Fan shaped and somewhat serrated.
*Color.*—Outer petal—Crimson, more-or-less Red Group 53A. Base—Crimson but less brilliant. Inside petal—The same as outer petals. Reverse side—Crimson, Red Group 53B.
*Appearance.*—Satiny and velvety.
*Texture.*—Soft.
Petaloids: About 5 in number.
*Size.*—About half the size of normal petals.
*Color.*—Crimson.
Peduncle: Of medium length, upright and Green in color.
Persistence: Petals hang on until fading begins.
Fragrance: Strongly fragrant when fully opened.
Effect of weather: Blooms are not affected by wet or hot weather.
Lasting quality:
*On plant.*—15 days.
As a cut flower.—7 to 10 days.
Disease resistance: Plant has good resistance for the ordinary diseases of carnations, particularly fusarium.

REPRODUCTIVE ORGANS

Stamen:
*Anthers.*—Random arrangement, 3 mm. long and averaging about 10 in number.
*Filaments.*—2.5 cm. long. Color—White with Crimson at top.
*Pollen.*—Yellowish in color.
Pistils: 2 in number, 3.5 cm. long.
*Stigmas.*—Light Crimson in color.
Ovaries: Globulous.

FRUIT

Fertility: The fruit is fertile.
Shape: Oblong.
Color: Green and Ochreous at maturity.

This variety of carnation plant most resembles the variety Pauline (unpatented) and its particular advantage is to be found in the unusually branched arrangement of the flower stems, and the brilliant solid red coloring of the medium-sized flat blossoms which appear on longer than ordinary stems and which are strongly fragrant when fully opened.

I claim:

1. The new and distinct variety of carnation plant substantially as herein shown and described, characterized by the unusual spray arrangement of blossoms appearing on relatively long stems branching from a strong, upright stalk, the absence of splitting, and the deep crimson color of its very fragrant flowers.

No references cited.

ROBERT E. BAGWILL, Primary Examiner